United States Patent [19]

Kassis et al.

[11] Patent Number: 4,977,288
[45] Date of Patent: Dec. 11, 1990

[54] M-AMINOPHENYLTRIALKYLSTANNANE

[75] Inventors: Amin I. Kassis, Chestnut Hill; Leslie A. Khawli, Newton Centre, both of Mass.

[73] Assignee: President and Fellows of Harvard College, Cambridge, Mass.

[21] Appl. No.: 150,131

[22] Filed: Jan. 29, 1988

[51] Int. Cl.$^5$ ............................................. C07F 7/22
[52] U.S. Cl. ..................................... 556/87; 548/103; 424/9
[58] Field of Search ................. 548/303, 103; 556/87; 564/412, 442

[56] References Cited

PUBLICATIONS

Eaborn et al., J Chem Soc. (B), 1967, p. 1036.
Visser et al., J Labelled Compounds and Radiopharmaceuticals XVII(5), p. 657 (1980).
Narula et al., "Method of Radiohalogenation of Protein . . . ", J. Nucl. Med. 28, 725 (#715) 1987.
Srivastava et al., "Design and Synthesis of a New N-(-p-[$^{125}$I]Iodophenyl)-Maleimide ([$^{125}$I]) PM)", J. Nucl. Med 28, 726 (#717( 1987.
Srivastava et al, "N-(p-Iodophenyl)Maleimide . . . )", J. Nucl. Med. 27, 1047 (#697) 1986.
Hnatowich et al., J. of Nuclear Med., vol. 28, pp. 1294-1302 (1987).
Livaniou et al., J. of Nuclear Med., vol. 28, pp. 1430-1434 (1987).
Wursthorn et al., J. of Organometallic Chemistry, vol. 140, pp. 29-39 (1977).
D. S. Wilbur et al., J. Nuclear Medicine, vol. 27, 959 (No. 335) (1986).
D. S. Wilbur et al., Poster from Sixth International Symposium on Radiopharmaceutical Chemistry, Boston, Jun. 1986.
S. Wilbur et al., Poster and Abstract from Second International Conf. on Monoclonal Antibody Immunoconjugates for Cancer, Mar. 1987.
M. Hylarides et al., J. Nuclear Medicine, vol. 28, 560 (No. 14) (1987).
S. W. Hadley et al., J. Nuclear Medicine, vol. 28, 725 (No. 7612).
Zalutsky et al., Appl. Radiat. Isotopes, vol. 38, No. 12, 1051-1055 (1987).
An Improved Method for the Radiohalogenation of Monoclonal Antibodies, Zalutsky et al., from: Immunological Approaches to the Diagnosis and Therapy of Breast Cancer, edited by Roberto L. Ceriani (Plenum Publishing Corp., 1987).
European Patent Application Publication EP 0203764 A2—Wilbur et al., (published Dec. 3, 1986).

Primary Examiner—Sam Rosen
Attorney, Agent, or Firm—Fish & Richardson

[57] ABSTRACT m-Radiohalo-aniline is a stable intermediate for preparing biotin-m-radiohalo-anilide to be used as an imaging agent or therapeutic agent. The invention also contemplates m-aminophenyltrialkylstannane which can be radiohalogenated and linked to biotin.

1 Claim, No Drawings

M-AMINOPHENYLTRIALKYLSTANNANE

This invention was made with Government support and the U.S. Government has certain rights in the invention under Contract No. DE-FG02-86-ER-60460 with the Department of Energy.

This invention relates to radiohalogenated biotin derivatives for use as a physioloqical imaging agent or therapeutic agent and to an intermediate radiohalogenated compound useful for making such agents.

It has previously been proposed to employ an avidin-antibody complex and $^{111}$Indium-labelled biotin in conjunction with each other as imaging agents: Hnatowich et al., J. of Nuclear Med., Vol. 28, 1294–1302 (1987). However, the very long half life of $^{111}$Indium presents disadvantages for many applications and it would be desirable to employ a radiohalogen-labelled biotin for imaging and therapeutic purposes.

It has also been proposed to label biotin by connecting it through an amide linkage to radioiodinated tyramine as taught in Livaniou et al., J. of Nuclear Med., Vol. 28, 1330–1334 (1987). Unfortunately, tyramine is enzymatically unstable and is cleaved rapidly in vivo leading to non-specific binding as well as to loss of intensity at the target site. Other amino compounds which are readily halogenated and which could also be linked to biotin through an amide linkage are known such as p-aminophenyltrimethylstannane which is taught, for example, by Wursthorn et al., J. of Organometallic Chemistry, Vol. 140, 29–39 (1977) but this compound is unstable resulting in poor yields during synthesis and decomposition during halogenation.

It has now been found that m-aminophenyl trialkylstannanes having the structure

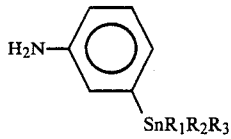

where $R_1$, $R_2$ and $R_3$ are alkyl groups having from 1 to 10 carbon atoms can readily be prepared in high yield and can easily be radiohalogenated to replace the trialkylstannane group with radiohalogen either before or after cross-linking with biotin. The compound is highly stable, in contrast to the corresponding para isomer, and both the linkage with biotin and the radiohalogenation can readily be carried out by conventional procedures.

The resulting radiohalogenated biotin derivatives having the structure

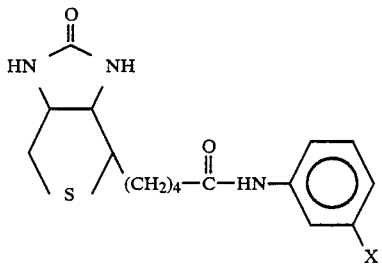

where X is a radiohalogen atom, preferably iodine or astatine, is also highly stable and retains its capacity to bond strongly and specifically to avidin, making it useful as an imaging or therapeutic agent in procedures such as those described by Hnatowich et al., supra.

The compounds of the present invention can be designated generically by the structure

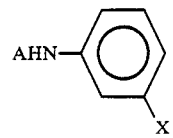

in which A is hydrogen or

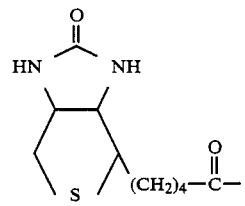

and X is $-SnR_1R_2R_3$ where $R_1$, $R_2$ and $R_3$ are alkyl groups having from 1 to 10 carbon atoms or X is a radiohalogen atom.

The m-aminophenyltrialkylstannane can be prepared by reacting m-bromoaniline with hexaalkyalkylditin in the presence of tetrakis (triphenylphosphine) palladium catalyst, the product being readily purified by chromatograghy to give a yield upwardly of 80% of the theoretical.

Radiohalogenation of the m-aminophenyltrialkylstannane can readily be accomplished by a conventional reaction with an alkali metal radiohalide and N-chlorosuccinimide. Any desired radiohaloqen including isotopes of chlorine and bromine can be employed, those preferred being isotopes of iodine and of astatine.

The m-aminophenyltrialkylstannane or the corresponding m-radiohalogenated aniline can be covalently linked to biotin by an amide linkage between the amino group and the carboxyl group of biotin via a conventional isobutyl chloroformate intermediate reaction product. The biotinyl m-radiohalo- anilide is particularly advantageous as an imaging and therapeutic agent when used in conjunction with an avidin-antibody complex which binds to a specific sight such as a tumor. The low cleavage rate of the m-analide in vivo coupled with the high clearance rate of biotin in vivo will assure minimal non-specific binding and rapid elimination of radioactivity from the body except in the desired specific bindinq sites.

The following specific examples are intended to illustrate more fully the nature of the invention without acting as a limitation upon its scope.

EXAMPLE 1 m-Aminophenyltributylstannane

A mixture of m-bromoaniline (1.26 g, 7.3 mmol), hexabutylditin (5.20 g, 8.9 mmol) and tetrakis phosphine)palladium (79.0 ml, 0.07 mmol) in toluene (10 mL) was stirred and heated to 105° C. for 12 hours under nitrogen atmosphere. As the reaction proceeded, the mixture turned to black. The resulting black mixture was filtered, and the filtrate obtained was evaporated to dryness under reduced pressure at 50° C. The residue obtained was dissolved in hexane and the solution was applied to a flash chromatography column (30 mm×200 mm) of Kieselgel 60, 230–400 mesh. Elution was initiated with hexane (100 mL, giving fractions 1–10) followed be 2% ethyl acetate in hexane (100 mL, giving fractions 11–20) and 4% ethyl acetate in hexane (200 mL, giving fractions 21–40). All fractions were analyzed by thin layer chromatography (TLC) on silica gel GHLF developed by UV and iodine fumes, and also visualized using 5% phosphomolybdic acid in ethanol, where $R_f$ values are for EtOAc/hexane (4:100). Fractions 3–10 contained hexabutylditin; $R_f$ 0.8, while fractions 32–40 contained starting material m-bromoaniline $R_f$ 0.25. Fractions 18–30, which showed a single spot at $R_f$ 0.4, were combined and the solvent were evaporated off to provide pure m-aminophenyltributylstannane (2.3 g, 82%): $^1$H NMR (CDCl3, δ); 7.2 (triplet, 1H, J=7 Hz, aryl C5-H); 6.9 (doublet, 1H, J=7 Hz, aryl C4-H); 6.8 (singlet, 1H, aryl C2-H)-; 6.6 (doublet, 1H, J=7 Hz, aryl C6-H); 3.6 (singlet, 2H, NH2); 0.9–1.7 (multiplets, 27H, 3×n-C4H9). Analysis calculated for $C_{18}H_{33}NSn$: C, 56.57; H, 8.70; N, 3.66. Found: C, 56.56; H, 8.72; N, 3.72.

EXAMPLE 2 m-Iodoaniline

To a stirred solution of sodium iodide (30 mg, 0.26 mmol) in H20 (100 μL), was added m-aminophenyltributvlstannane (100 mg. 0.26 mmol) in methanol (1 mL), followed by a solution of N-chlorosuccinimide (NCS) (35 mg, 0.26 mmol) in methanol (1 mL). Reaction progress was followed by TLC, where starting material stannane with EtOAC/hexane, 2:1 shows $R_f$ 0.58. The reaction mixture was stirred at room temperature for 30 minutes The mixture initially turned yellow from the formation of I+. The solution rapidly became lighter until a colorless solution resulted. To this was added a minimum amount of 5% aqueous sodium bisulfite and the resulting mixture was evaporated and chromatographed on e 60 230–400 mesh using a 1×20 cm disposable column (BioRad). Elution was initiated with hexane (9 mL, giving fractions 1–3) followed by 33% ethyl acetate in hexane (27 mL, giving fractions 4–12). Fractions 6 and 7 were combined and the solvent was removed in vacuo to give the desired product m-iodoaniline (54 mg, 94%): TLC (EtOAC/hexane, 1:2) $R_f$ 0.43; $^1$H NMR (CDCl3, δ); 6.6–7.1 (multiplets, 4H, 4 aryl CH), 3.6 (singlet, 2H, NH2).

EXAMPLE 3 m-[$^{125}$I]iodoaniline

In a 5M1 test tube containing sodium [$^{125}$I] iodide (10.5 μCi) was added 20 μL of a 330 mM solution of the stannane of Example 1 in methanol. To this was added 50 μL of 72 ml solution of N-chlorosuccinimide in methanol. The reaction was stirred vigorously for 30 minutes at room temperature and quenched with 5% aqueous sodium bisulfite. The resulting mixture was evaporated under a stream of nitrogen and chromatoqraphed on Kieselgel 60 230–400 mesh using a 8×100 mm disposable column (BioRad). Elution was in.tirated with hexane (5 mL, giving fractions 1–5) followed by 35% ethyl acetate in hexane (15 mL, giving fractions 6–20). Fractions 10–13 showed one spot on TLC autoradiography and indicated that the radioactivity comigrated with radioinert m-iodoaniline, by using EtOAC/hexane (1:2), $R_f$ 0.43. The desired fractions were combined and measured using a radioisotope calibrator to give 9.4 μCi of m-[$^{125}$I]iodoaniline (90% radiochemical yield). Fractions 5–8 constituted 5% of the radioactivity containing products and was accounted for by two compounds with $R_f$ values 0.60 and 0.74. The identity of the side products was not determined.

EXAMPLE 4

A solution of biotin (220 mg, 0.90 mmol) in 7 mL anhydrous dimethyl formamide (DMF) was stirred and cooled by a salt ice bath. Triethylamine (0.14 mL, 1.05 mmol) was added followed by isobutyl chloroformate (0.13 mL, 1.05 mmol) giving a white precipitate. After 10 min., m-iodoaniline (200 ml, 0.90 mmol) dissolved in DMF (0.5 mL) was added, stirring was continued for 5 minutes at salt-ice bath temperature, then the bath was removed, and the mixture was allowed to stir or 15 minutes at room temperature. The resulting mixture was evaporated under reduced pressured at 70° C. and 0.3 mL of 5% sodium bicarbonate was added. The residue obtained was dissolved in chloroform and applied to a flash chromatography column (30×200 mm) of Kieselgel 60, equilibrated with CHCl3/EtOAc (3:1). Elution was initiated with the same solvent system (80 mL, giving fractions 1–8) followed by CHCl3/EtOAc/MeOH (3:1:1) (120 mL, giving fractions 9–20). All fractions were analyzed by TLC, where $R_f$ values are reported in CHCl3/EtOAc/MeOH (3:1:1). Fractions 3–6 contain a side product identified as isobutyl-N-m-iodophenylcarbonate; $R_f$ 0.89, while fractions 7–11 contained starting material m-iodoaniline; $R_f$ 0.81. Fractions 13–17 which showed a single spot at $R_f$ 0.51, were combined and the solvent was evaporated off to give pure biotinyl-m-iodoanilide (285 mg, 71%): m.p. $^1$H NMR (Me2SO-d6, δ), 1.5 (multiplets, 8H); 2,3 (multiplets, 2H) 2.8 (multiplets, 1H); 4.3 multiplets, 2H); 6.4 (broad singlet, 2H); 6.9–8.1 (muliplets, 4H, 4 aryl CH); 9.8 (singlet, 1H, NH).

Analysis calculated for $C_{16}H_{20}N_3O_2SI$: C, 43.15; H, 4.52; N, 9.43. Found: C, 42.66; H, 4.61; N, 9.62

EXAMPLE 5

Biotinyl-m-[$^{125}$I]iodoanilide

A solution of 10 ml biotin in 1 mL of anhydrous DMF was cooled in salt-ice bath. Triethylamine (6 μL) was added followed by isobutyl chloroformate (6 μL). After 10 minutes, m-[$^{125}$I]iodoaniline (4.1 μCi) dissolved in 50 μL of DMF was added, and the mixture was stirred vigorously for 15 minutes at room temperature and quenched with 50 μL of 5% aqueous sodium bicarbonate. The resulting mixture was chromatographed on Kieselqel 60 using a 8×100 mm disposable column (BioRad). Elution was initiated with CHCl3/EtOAc (3:1) (10 mL, giving fractions 1–5) followed by CHCl3/EtOAc/MeOH (3:1:1) (12 mL, giving fractions 6–16). Fractions 8–10 showed one spot autoradiography and indicated that the radioactivity comigrated with radioinert biotinyl-m-iodoanilide, by usinq CHCl3/EtOAc/MeOH (3:1:), $R_f$ 0.51. The desired fractions were combined to give 0.83 μCi of biotinyl-m-[$^{125}$I]iodoanilide (80% radiochemical yield). Fraction 4 constituted 6% of the radioactivity containing products and was accounted by a side product with $R_f$ value 0.89.

Similar results can be obtained using other alkali metal halides and radiohalides and using other hexaalkyl ditin compounds.

What is claimed is:

1. m-Aminophenyltribuytlstannane.

* * * * *

UNITED STATES PATENT AND TRADEMARK OFFICE
CERTIFICATE OF CORRECTION

PATENT NO. : 4,977,288

DATED : December 11, 1990

INVENTOR(S) : Amin I. Kassis, et. al.

It is certified that error appears in the above-identified patent and that said Letters Patent is hereby corrected as shown below:

On the Title page

In the References Cited

In the 13th cite, "(No. 7612)" should be --(No. 712)--

Col. 4, line 67, "m-Aminophenyltribuylstannane" should be --m-Aminophenyltributylstannane--

Signed and Sealed this

First Day of September, 1992

*Attest:*

DOUGLAS B. COMER

*Attesting Officer*     Acting Commissioner of Patents and Trademarks